Figure 1:
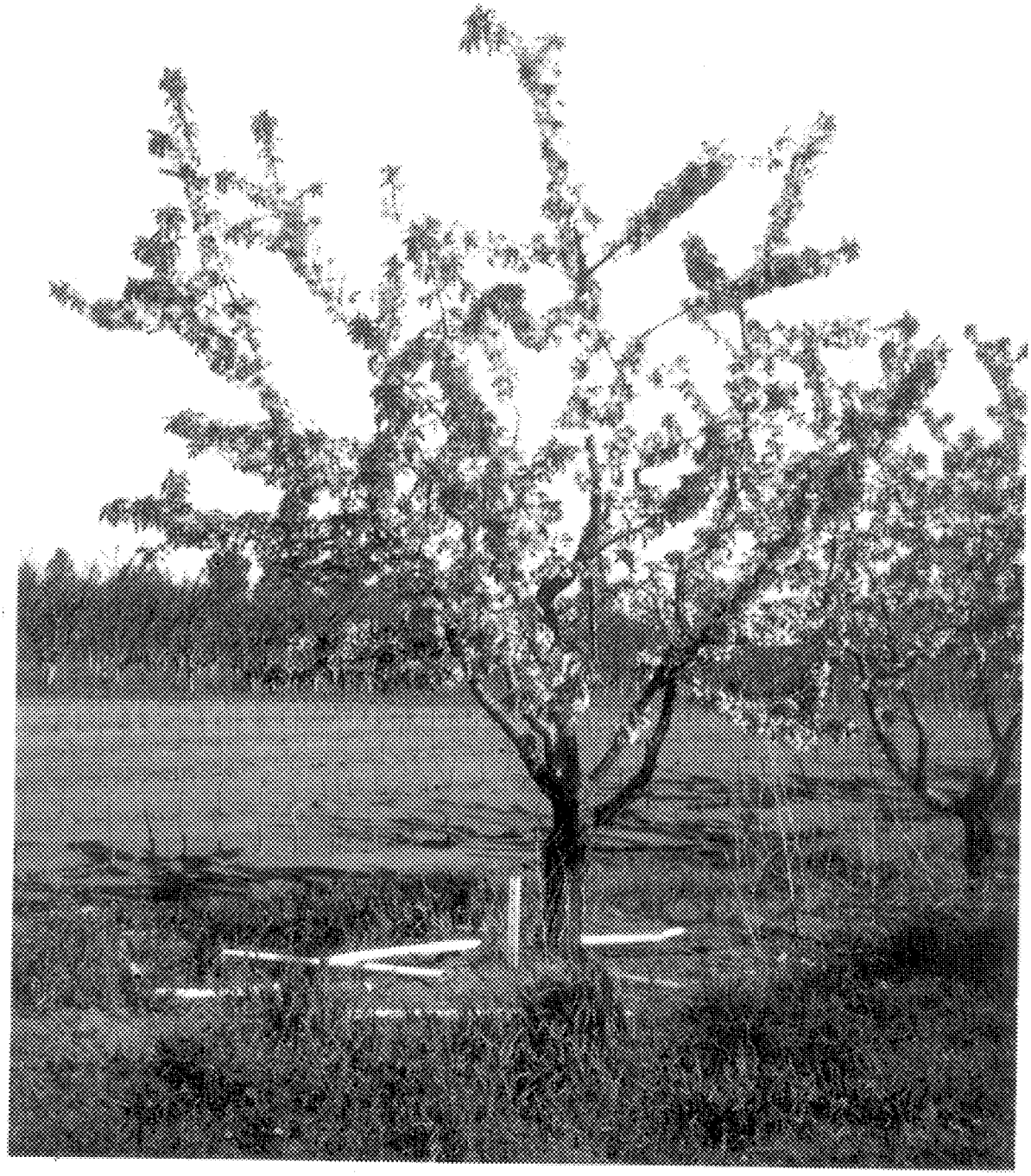

US00PP11378P

United States Patent [19]

Lane

[11] Patent Number: Plant 11,378

[45] Date of Patent: May 9, 2000

[54] CHERRY TREE NAMED 'SUMLETA'

[75] Inventor: W. David Lane, Summerland, Canada

[73] Assignee: Okanagan Plant Improvement Co. Ltd., Summerland, Canada

[21] Appl. No.: 09/104,278

[22] Filed: Jun. 25, 1998

[51] Int. Cl.[7] ..... A01H 5/00

[52] U.S. Cl. ..... Plt./181

[58] Field of Search ..... Plt./181

[56] References Cited

U.S. PATENT DOCUMENTS

P.P. 8,721 5/1994 Calder ..... Plt./181
P.P. 9,857 4/1997 Nies ..... Plt./181

*Primary Examiner*—Howard J. Locker
*Assistant Examiner*—Wendy A Baker

[57] ABSTRACT

A new and distinct variety of cherry tree, originating from a controlled cross of 'Lapins'×'2N-39-5' made in 1976 is described. The resulting seedling was established in a selection block in 1985 and given the breeder's reference number '13N-6-59'. The variety has been established and is being maintained at the research facility. Evaluations began upon fruiting. The variety is stable with no variations occurring, and demonstrates qualities of the tree, flower, and fruit that in combination make the variety significantly different from from its parents and other fruiting cherry varieties, in that 'Sumleta' has large kidney shaped fruit, with shiny, mahogany skin with fine light dots and dark red flesh. The fruit has a prominent suture and a hollow apex with and obvious dimple. The fruit matures mid season, about 5 to 6 days after 'Van' and 'Bing' and 4 to 5 days before 'Lapins'. The fruit is very firm, has a sweet taste with some astringency, and is moderately susceptible to rain splitting. The stone of 'Sumleta' is round in lateral view, medium to large in size, and has moderately developed keel. The tree is upright, self-compatible, and moderately vigorous and has produced good crops annually since fruiting commenced. The variety was named 'Sumleta' in 1995.

5 Drawing Sheets

BACKGROUND OF THE INVENTION

Field of Invention

| | |
|---|---|
| Name: | 'Sumleta' |
| Synonym: | 'Sonata' |
| Breeders Reference Number | '13N-6-59' |
| Genus: | *Prunus* |
| Species: | *avium* |
| Type: | Fruiting sweet cherry |
| Market Use: | Dessert quality cherry |

This invention relates to cherry trees and particularly to a seedling cherry tree from a controlled cross made by Dr. W. David Lane of the Pacific Agri-Food Research Centre Summerland cherry breeding program located at Summerland, British Columbia, Canada.

The Agriculture and Agri-Food Canada research facility at Summerland was established in 1914. Originally called the Dominion Experimental Farm at Summerland, the name was changed to the Summerland Research Station in 1959, the Summerland Research Centre in 1994 and to the Pacific Agri-Food Research Centre (PARC) Summerland in 1996. The tree fruit breeding program was established in 1924 to provide new varieties for the tree fruit industry of British Columbia, Canada, and the world. The breeding program at Summerland has produced several tree fruit varieties including 'Spartan' (unpatented), 'Summerred' (unpatented), and 'Sunrise' (unpatented), apples and 'Van' (unpatented), 'Lapins' (unpatented), and 'Sweetheart' (unpatented) sweet cherries. The tree fruit breeders typically produce several thousand seedlings each year.

The three broad objectives of the cherry breeding program are: 1) to diversify the product to allow growers to take advantage of niche markets; 2) to improve environmental adaptation to major fruit growing areas, for consistent production of high quality fruit; 3) to reduce the cost of production. The varieties are evaluated for the following traits to insure that the objectives are met. Primary traits include: early onset of bearing, self-compatibility, extended ripening season, fruit size, fruit firmness, and resistance to cracking. Secondary traits include: disease resistance, winter hardiness, resistance to spring frosts, and compact tree growth habit.

Upon fruiting, the seedlings are evaluated for fruit and tree quality. Bloom and harvest indices, disease susceptibility and growth habit are evaluated in the field. Promising seedlings are re-propagated by budding or grafting onto rootstocks, and planted out as first selections in variety evaluation plots. The reproductions are evaluated for varietal stability, disease susceptibility, and fruit and tree quality. The most promising selections are re-propagated again and planted out in randomized evaluation plots complete with reference varieties (commercial varieties). Upon fruiting, selections are evaluated for varietal stability in the field, and for fruit quality, in "in-house" sensory evaluation panels. The new varieties are compared to reference varieties to establish uniqueness.

The present invention relates to a new and distinct variety of cherry tree which was named 'Sumleta' in 1995. The original cross was made in 1976 by breeder Dr. W. David Lane. The variety is the offspring of the seed parent 'Lapins' and the pollen parent '2N-39-5' (unpatented) (a 'Van'× 'Stella' cross from the summerland program). The variety was planted out as a seedling and given the Breeders Reference Number '13N-6-59' in 1985.

Distinguishing Characteristics

Under growing conditions at the Pacific Agri-Food Research Centre (PARC) Summerland located at Summerland in the Okanagan Valley of British Columbia, Canada, the variety 'Sumleta' consistently has the following characteristics. The variety is a self-compatible, mid-season cherry maturing about 6 or 7 days after 'Van' and 'Bing' and 4 to 5 days before 'Lapins'. The fruit of 'Sumleta' is kidney shaped and has medium-long, thick stems. The fruit has mahogany-colored skin with a brilliant luster, dark red flesh, and a slightly astringent taste. The fruit is very large and firm averaging 12.7 g in weight and a rating of 77 in firmness as measured by Shores Durometer. It is moderately resistant to rain splitting. The fruit has a prominent suture and a distinctive prominent hollow apex (blossom end). The stone of 'Sumleta' is medium in size (averaging about 10 mm in diameter) and is medium relative to the size of the fruit. The stone is round in the lateral and basal views and elliptic in frontal view. The keel development is moderate.

The leaves of 'Sumleta' have weak glossiness on the upper side, are elliptical in shape and have shallow to medium depth, serrate margins. The leaves are oriented obliquely downwards in relation to the shoot and have acute tips and rounded bases. The petioles are long (over 2.5 cm), have anthocyanin coloration on both sides and have two to four red kidney-shaped nectaries at the base.

'Sumleta' flowers in the middle of the blossom season, with 'Bing', 1 to 2 days after 'Van', and 3 to 4 days after 'Lapins'. The variety is self-compatible. The flowers are white, medium in size, single in type, and appear in clusters. The petals are small, broad elliptic in shape and overlapping.

The tree of 'Sumleta' is of moderate vigor and hardy to Zone 6A. The tree is precocious, and productive, and has produced good crops annually since first fruiting. The one-year-old dormant shoots show little or no anthocyanin coloration and are of medium to thick diameter at the middle of the shoot (averaging about 6.5 mm). On average the internodes are medium to long (averaging about 41 mm) and have a few to a medium number of lenticels. The buds on the one year old dormant shoots are ovate and are slightly held out in relation to the shoot.

Parent Plants

'Sumleta' is the result of a controlled cross of the seed parent 'Lapins' and the pollen parent '2N-39-5' (unpatented) made in 1976.

'Lapins' is a result of a controlled cross of the seed parent 'Van' and the pollen parent 'Stella' made at the Pacific Agri-Food Research Centre in 1965.

'2N-39-5' is a result of a controlled cross of the seed parent 'Van' and the pollen parent 'Stella' made at the Pacific Agri-Food Research Centre, Summerland in 1965. '2N-39-5' was not of commercial quality and was dropped from the program. The variety was used as parent because of its potential to pass on self-fertility.

The fruit of 'Sumleta' matures 6 to 7 days after 'Van' and 4 to 5 days before 'Lapins'. 'Sumleta' fruit is kidney-shaped, has a hollow apex end and obvious dimple, and a prominent suture, whereas 'Lapins' is flat to round in shape, flat at the apex and has a non-prominent suture. The stone of 'Sumleta' is round in lateral view, medium to large in size, and has moderately developed keel. The stone of 'Lapins' is narrow elliptic in lateral view, large, with a undeveloped keel. The tree habit of 'Sumleta' is upright and moderately vigorous while the tree habit of 'Lapins' is upright and very vigourous.

SUMMARY OF THE INVENTION

The new and distinct variety of *Prunus avium* fruiting cherry tree, 'Sumleta', resulted from a controlled cross made in 1976 at the Pacific Agri-Food Research Centre in Summerland, British Columbia, Canada by breeder Dr. W. David Lane. The resulting seedling was established in a selection block in 1985 and given the breeder's reference number '13N-6-59'. The variety has been established and is being maintained at the research facility. Evaluations began upon fruiting.

The variety is stable with no variations occurring, and demonstrates significant differences from its parents and other fruiting cherry varieties in that the fruit of 'Sumleta' matures about the middle of cherry season is large and firm with a hollow apex and distinctive obvious dimple at the blossom end. The skin of 'Sumleta' is mahogany in color and highly lustrous with fine light colored highlights. The flesh is dark red. The fruit is sweet (19% soluble solids) with some astringency and medium acidity (595 titratable units). The fruit is moderately susceptible to rain splitting (42% natural rain splits). The stone of 'Sumleta' is round in the lateral view and has a moderately developed keel. The tree habit is upright, somewhat spreading, and moderately vigorous. The variety was first propagated in 1985 by budding on Mazzard F12/1 rootstock was established in a second selection field at the Pacific Agri-Food Research Centre at Summerland, British Columbia, Canada in 1987.

BRIEF DESCRIPTON OF THE DRAWINGS

The accompanying photographs show various characteristics of the cherry variety 'Sumleta'.

In FIG. 1 a typical tree is shown. This Figure shows the growth habit of the tree, approximately 7 years old, at bloom.

Figure 2:
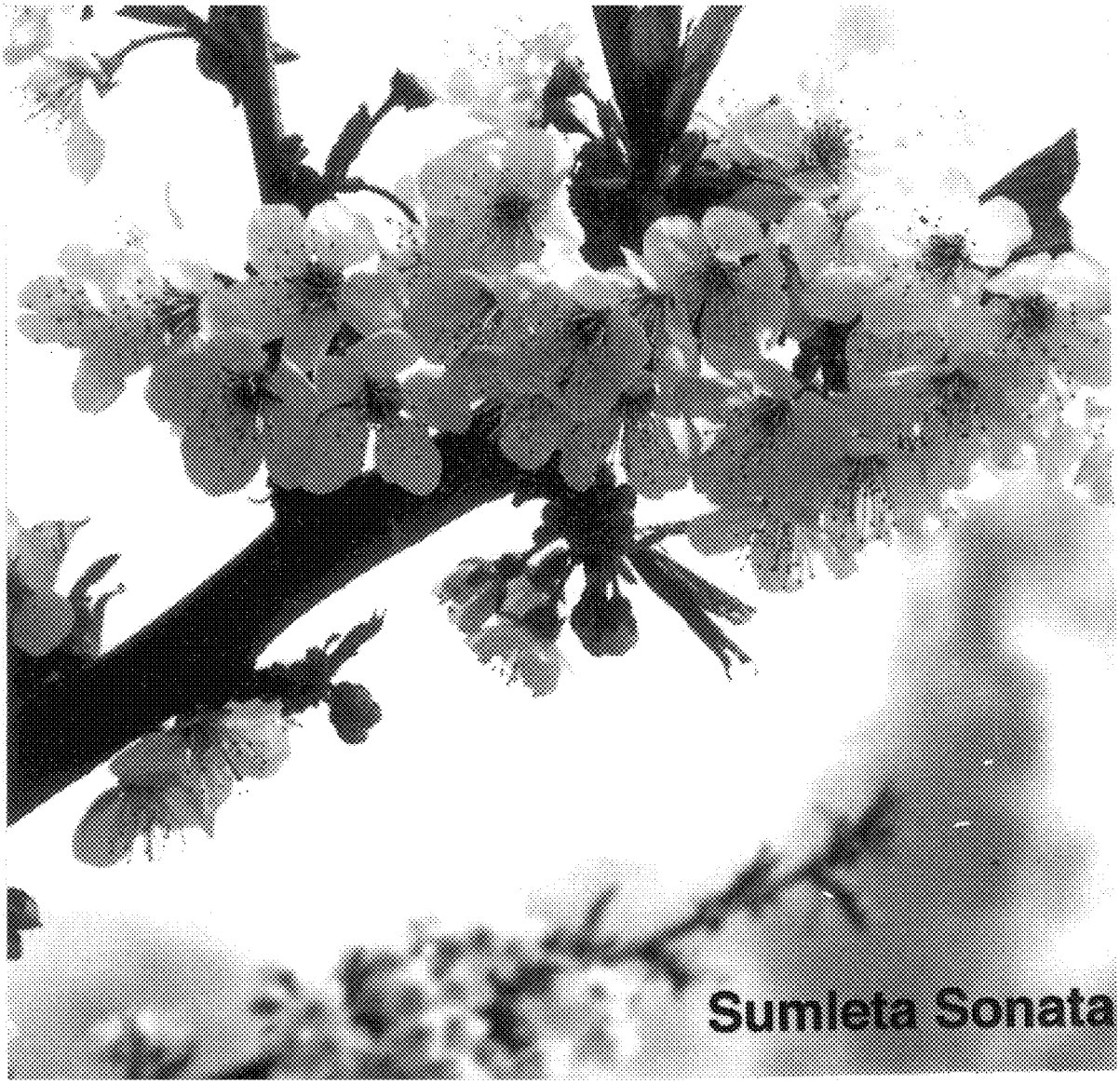

In FIG. 2 a typical branch at blossom is shown. The figure displays the blossoms of 'Sumleta' at about full bloom.

Figure 3:
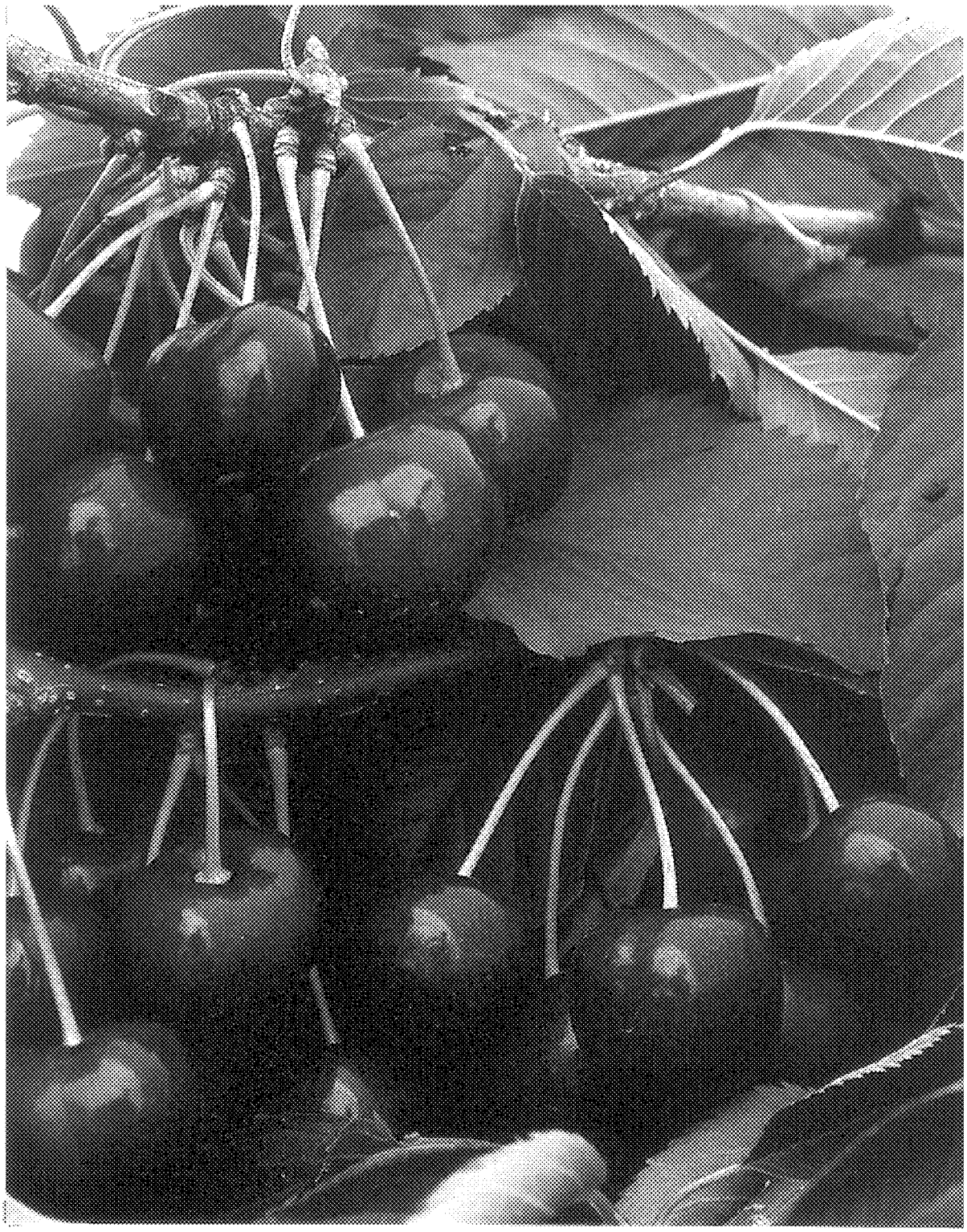

FIG. 3 shows a typical branch with fruit somewhat prior to harvest. This figure illustrates the cluster of fruit and the leaves of the variety.

Figure 4:
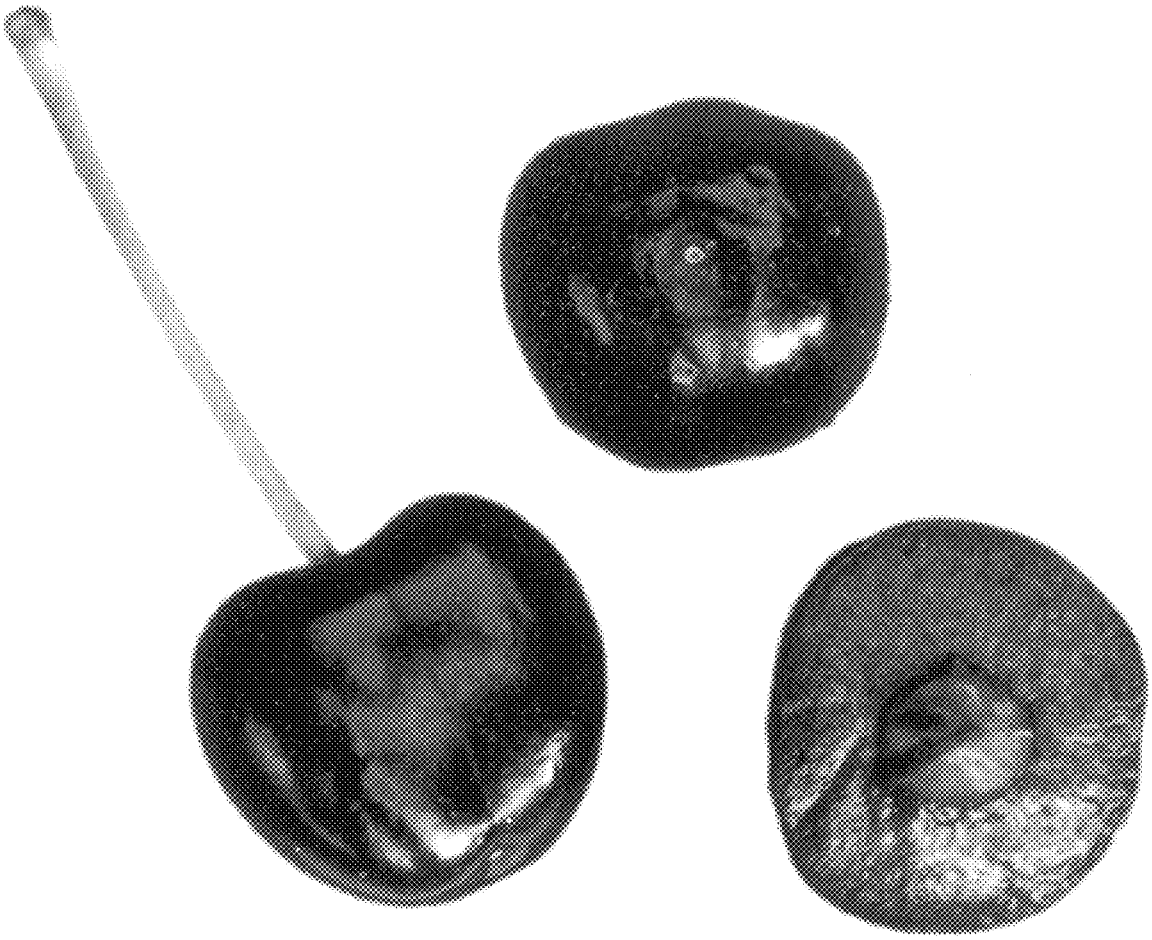

FIG. 4 illustrates the mature fruit of 'Sumleta' in large scale. The fruit is arranged to display the blossom end (top) and the side view (middle left) of the fruit. These views show the color of the fruit at maturity in the middle right the fruit is displayed in cross section after being cut centrally across the midline. The flesh color and the arrangement of the flesh in relation to the stone is displayed.

Figure 5:
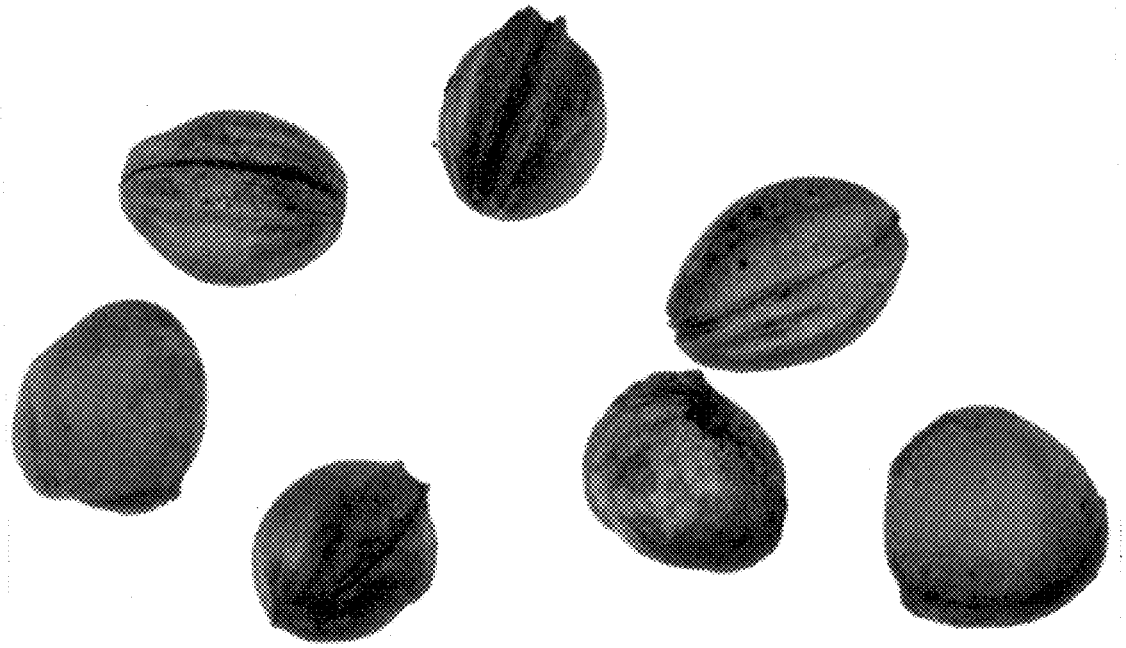

FIG. 5 shows various views of the stone of the fruit, after drying and the flesh is removed. The basal, lateral and front views are displayed as well as views of the keel. All colors as set forth in the specification refer to those set forth by The Royal Horticultural Society Colour Chart (R.H.S.). Colors as shown are as close as is possible to attain in a color illustration of this character.

TRIALS AND EVALUATIONS

A seedling resulting from a controlled cross made in 1976 was planted into a seedling block and given the Breeders' Reference Number '13N-6-59' in 1985. '13N-6-59' was reproduced and planted in cultivated variety blocks, complete with standards at the Pacific Agri-Food Research Centre (PARC), Summerland orchards in 1985. The reproductions have shown 'Sumleta' ('13N-6-59') to be stable with no variations occurring. The variety has been observed and evaluated since first fruiting.

Test plots established at PARC Summerland consisting of 4 trees of 'Sumleta' ('13N-6-59') were established in 1987. The variety was compared to the reference varieties 'Bing'

(unpatented), 'Van', and 'Lapins' of approximately the same age and planted in the same area. Controlled grower trials, under test agreements, have been established in British Columbia and in selected sites in the United States.

'Sumleta' was evaluated for fruit size, fruit firmness, maturity date, fruit taste (soluble solids and titratable acids), natural rain splits, tree growth habit, fruit shape, productivity, prococity and disease resistance from first fruiting in 1985 until the present.

Under growing conditions at the Pacific Agri-Food Research Centre (PARC) Summerland located at Summerland in the Okanagan Valley of British Columbia, Canada, the variety 'Sumleta' consistently has the following characteristics. 'Sumleta' has larger average fruit size (12.7 g.) than 'Van' (8.7 g) 'Bing' (9.0 g.) and 'Lapins' (10.6 g.). The variety matures on average 6 to 7 days later than 'Van' and 'Bing' and 4 to 5 days earlier than 'Lapins'. 'Van' and 'Bing' mature on average about the first week of July in Summerland. The flesh is significantly more firm than 'Bing' and is as firm as 'Van' and 'Lapins'. 'Sumleta' averages a rating of 77 in firmness as measured by Shores Durometer, 'Bing' has a rating of 70, 'Van' 78 and 'Lapins' 76. The fruit of 'Sumleta' on average is as sweet as 'Van' and 'Bing' and sweeter than 'Lapins' and has more titratable acids than 'Van' and 'Lapins' (no measurements were taken for 'Bing'). 'Sumleta' has a slightly more astringent taste than the refence varieties. 'Sumleta' has a slightly higher tendency to rain split than 'Van' and significantly higher rain splitting tendency than 'Bing' and 'Lapins'. In controlled cracking index trials in the laboratory. 'Sumleta' is significantly more prone to splitting than 'Van' or 'Lapins' (no trials were done on 'Bing'). 'Sumleta'has a prominent suture and hollow spex which are not evident in the reference varieties. 'Bing' and 'Van' have more pointed apices and 'Lapins' has a flat apex. The stone of 'Sumleta' has a moderately developed keel as does 'Bing' and 'Van'; the keel in 'Lapins' is undeveloped. The fruit of 'Sumleta' is kidney shaped and has medium-long, thick stems. 'Lapins' And 'Bing' are kidney-shaped while 'Van' is flat-round to round in shape. The stems of 'Van' are on average shorter than 'Sumleta' and 'Lapins' and 'Bing' are longer. The skin of 'Sumleta' is more lustrous than the reference varieties.

The leaves of 'Sumleta' have weak glossiness on the upper side, have shallow to medium depth, serrate margins. 'Lapins' has very glossy leaves and medium depth, dentate margins. The leaves of 'Sumleta' oriented obliquely downwards in relation to the shoot, whereas 'Bing' leaves are horizontal. The petioles have anthocyanin coloration on both sides (anthocyanin coloration is absent in 'Lapins') and have 2 to 4 nectaries at the base. On average 'Lapins' has 2 to 4 nectaries while 'Van' and 'Bing' have 2.

'Sumleta' flowers in the middle of the blossom season, with 'Bing', 1 to 2 days after 'Van', and 3 to 4 days after 'Lapins'. 'Sumleta' is self-compatible, as is 'Lapins' while 'Van' and 'Bing' are not. The flowers are white, medium in size, single in type, and appear in clusters. 'Lapins' has a slightly larger flower and 'Van' a slightly smaller flower. The petals of 'Sumleta' are small and overlapping. 'Van' and 'Bing' have large partially overlapping petals and 'Lapins' has petals that are medium-sized and touching.

The tree of 'Sumleta' is upright somewhat spreading and has moderate vigor while 'Lapins' is upright and vigorous. The attitude of the one-year-old shoots is upright while 'Van' and 'Bing' are horizontal. The shoots, on average, are of medium to thick diameter, slightly larger than 'Lapins' which in turn is slightly larger than 'Van'. The internodes of 'Sumleta' are, on average, longer than 'Lapins' and shorter than 'Van'. The buds on the one year old shoots are slightly held out in relation to the shoot, while the buds of 'Lapins' are clearly held out. 'Bing' has appressed buds.

Virus Status and Disease Susceptibility/Resistance

Wood of Sumleta is being virus indexed at the Centre for Plant Health at Sidney B.C. Upon release of certified material Virus Certified trees will be established and maintained at the okanagan Plant Improvement Companies certified budwood orchard at Summerland, B.C.

Sumleta has shown no unusual susceptibility nor resistance to any plant or fruit pests and/or diseases.

Pomological Characteristics
'Sumleta'

| | | |
|---|---|---|
| Fruit end use: | | Dessert |
| Group | | Sweet |
| All trees are of approximately the same age and have Mazzard F12/1 for rootstock. | | |
| Growth Characteristics: | | Observations are measurerments from 6 year old bearing trees |
| Tree vigor | | Moderate |
| Tree height | | Less than 7 m |
| Tree width | | Less than 7 m |
| Growth habit | | Upright |
| Branch pubescence | | Very slight |
| Bearing | | Annual and regular |
| Shoot Characteristics: | | Observations one-year old dormant shoots |
| Shoot attitude | | Erect |
| Wood bud shape | | Ovate |
| Position of bud | | Slightly held out |
| Number of lenticels | | Few to medium |
| Shoot diameter (middle of internode) | | |
| Mean: | | 6.5 mm |
| Range: | | 3 mm |
| Intemode length (middle of shoot) | | |
| Mean: | | 40.9 mm |
| Range: | | 35.7 mm |
| Anthocyanin coloration (shoot tip) | | Absent |
| Bark Coloration 1st year wood | | 165B (RHS) (at maturity) |
| Bark Coloration Mature Branch | | 199A (RHS) (at maturity) |
| Bark Coloration Trunk | | 166A (RHS) (at maturity) |
| Leaf Characteristics: | | Measurements are the mean of 10 leaves |
| Bud Burst | | Mid period as compared to other varieties |
| Attitude to shoot | | Oblique downwards |
| Leaf shape | | Elliptical |
| Angle at blade tip | | Acute |
| Shape of base | | U-shape |
| Shape of apex | | Cuspidate |
| Leaf color upper side | | 137A (RHS) |
| Leaf color lower side | | 147B (RHS) |
| Anthocyanin upper side | | Absent |
| Anthocyanin (leaf glands) | | Present |
| Glossiness | | Weak-medium |
| Margin indentation | | Serrate |
| Degree of indentation | | Shallow-medium |
| Leaf length | Mean | 14.3 cm |
| | Range | 5.5 cm |
| Leaf width | Mean | 6.3 cm |
| | Range | 1.8 cm |
| Blade ratio | Length/width | 2.3 |
| Petiole length | Mean | 3.3 cm |
| | Range | 2.2 cm |
| Petiole anthocyanin | | 59A |

-continued

| Pomological Characteristics 'Sumleta' | |
|---|---|
| Number of nectaries (out of 10) | 2–4 |
| Nectaries color | 45A (RHS) |
| FLOWER CHARACTERISTICS: | Measurements are the mean of 10 flowers |
| Bloom Period | 1–2 days after Van and with Bing |
| Flowers per cluster | 3 to 10 per cluster |
| Duration of Bloom | 5 to 7 days |
| Flowering density | Sparse to medium |
| Flower appearance | In clusters |
| Flower type | Single |
| Flower size | 34.6 mm |
| Pedicel length | 20.9 mm |
| Pedicel thickness | 1.3 mm |
| Petal size (length) | 12.7 mm |
| Petal shape | Broad elliptic |
| Petal position of margins | Overlapping |
| Petal color | 155D (RHS) |
| Anther color (at dehiscence) | Yellowish green |
| Frequency of supplementary pistil | Absent |
| Pistil presence | Normal pistil |
| Ovary pubescence | Absent |
| Fruit Characteristics: | Measurements are the means from a 10 fruit sample |
| Maturity date | 10–15th of July (at Summerland) |
| Weight (average) | 12.5 g |
| Large diameter | Average about 31 mm |
| Fruit length | Average about 26.5 mm |
| Shape | Kidney |
| Symmetry of fruit | Symmetrical |
| Position of largest diameter | Middle |
| Profile in lateral view | Rounded |
| Suture | Pronouneed |
| Fruit apex | Hollow (dimpled) |
| Color of flesh | 187B (RHS) |
| Color of skin | 187A (RHS) |
| Dots on skin | Fine (light color) |
| Glossiness | Brilliant luster |
| Firmness of flesh | 77 on shores durometer |
| Natural rain splits | Moderately susceptible (43%) |
| Skin cracking susceptibility | 63 (on cracking index) |
| Fruit taste | Sweet-tart |
| Juice color | 187C (black red) |
| Fruit juiciness | Medium |
| Soluble solids | 18.5% |
| Length of stalk | 3.5 cm |
| Stalk thickness | 1.6 mm |
| Adherence of flesh to stone | Not adherent |
| Stone Color | 165C (RHS) |
| Stone size | 9.9 mm |
| Shape in lateral view | Round |
| Stone size relative to fruit | Medium |
| Stone shape front view | Elliptic |
| Stone Keel | Medium developed |

-continued

| Pomological Characteristics 'Sumleta' | |
|---|---|
| Compatibility | Self-compatible |
| Fruit set (yield efficiency) | High annual cropping |
| Storage | At least 2 weeks at 0 degrees C. |
| Storage | At least 4 weeks in Modified Atmosphere Packaging |

Botanical Description of the Plant:

| | |
|---|---|
| Name: | 'Sumleta' |
| Genus: | *Prunus* |
| Species: | *avium* |
| Market Class: | Sweet dessert |
| Parentage: | 'Lapins' X '2N-39-5' |
| Name: | 'Lapins' |
| Genus: | *Prunus* |
| Species: | *avium* |
| Market Class: | Sweet dessert |
| Parentage: | 'Van' X 'Stella' |
| Name: | '2N-39-5' |
| Genus: | *Prunus* |
| Species: | *avium* |
| Market Class: | For breeding purposes only |
| Parentage: | 'Van' X 'Stella' |

We claim:

1. A new and distinct variety of cherry tree named 'Sumleta' originating from a controlled cross of 'Lapins'× '2N-39-5' substantially illustrated and described and distinguished from other varieties in that the fruit matures later than 'Van' and 'Bing' and earlier than 'Lapins', is very large, very firm, sweet and slightly astringent in taste, has shiny mahogany skin and dark red flesh, is kidney shaped with a prominent suture and hollow apex with an obvious dimple, is moderately resistant to rain splitting and is produced on a tree that is upright, self-compatible, moderately vigorous and produces good crops annually, that has leaves oriented obliquely downwards with medium depth, serrate margins and petioles that have anthocyanin coloration on both sides and two to four kidney-shaped nectaries at the base, and that flowers in the middle of the blossom season producing medium sized single type flowers arranged in clusters that have small, broad elliptic shaped and overlapping petals under growing conditions at Summerland, British Columbia, Canada.

* * * * *

Sumleta Sonata